United States Patent [19]

Rozen et al.

[11] Patent Number: 6,073,106
[45] Date of Patent: Jun. 6, 2000

[54] METHOD OF MANAGING AND CONTROLLING ACCESS TO PERSONAL INFORMATION

[75] Inventors: Michael J. Rozen, Palm Beach Garden, Fla.; Connie B. Doherty; Karen L. Chesko, both of Cincinnati, Ohio

[73] Assignee: NEHDC, Inc., Portland, Oreg.

[21] Appl. No.: 09/183,687

[22] Filed: Oct. 30, 1998

Related U.S. Application Data

[60] Provisional application No. 60/064,332, Oct. 30, 1997.

[51] Int. Cl.[7] .................................................. G06F 17/60
[52] U.S. Cl. ................................ 705/3; 705/2; 713/202; 707/9; 707/104
[58] Field of Search ............................ 705/2, 3, 51, 54; 707/9, 104; 709/229; 713/202

[56] References Cited

U.S. PATENT DOCUMENTS

| | | |
|---|---|---|
| 4,315,309 | 2/1982 | Coli . |
| 4,812,994 | 3/1989 | Taylor et al. ............................ 705/410 |
| 4,868,376 | 9/1989 | Lessin et al. . |
| 4,882,474 | 11/1989 | Anderl et al. ............................ 235/380 |
| 4,960,982 | 10/1990 | Takahira . |
| 4,984,272 | 1/1991 | McIlroy et al. . |
| 5,150,409 | 9/1992 | Elsner . |
| 5,301,246 | 4/1994 | Archibald et al. . |
| 5,325,294 | 6/1994 | Keene . |
| 5,327,341 | 7/1994 | Whalen et al. . |
| 5,465,082 | 11/1995 | Chaco . |
| 5,559,885 | 9/1996 | Drexler et al. . |
| 5,559,888 | 9/1996 | Jain et al. ................................. 380/25 |
| 5,572,422 | 11/1996 | Nematbakhsh et al. . |
| 5,629,981 | 5/1997 | Nerlikar . |
| 5,664,109 | 9/1997 | Johnson et al. ............................ 705/2 |
| 5,664,207 | 9/1997 | Crumpler et al. . |
| 5,772,585 | 6/1998 | Lavin et al. ............................ 600/300 |
| 5,832,488 | 11/1998 | Eberhardt . |
| 5,867,821 | 2/1999 | Ballantyne et al. ........................ 705/2 |
| 5,903,889 | 5/1999 | De la Huerga et al. .................... 707/3 |
| 5,996,715 | 10/1999 | Sweeney et al. ....................... 707/203 |

*Primary Examiner*—Allen R. MacDonald
*Assistant Examiner*—Hani M. Kazimi
*Attorney, Agent, or Firm*—ipsolon llp

[57] ABSTRACT

Via Internet communications or via phone/fax/mail, a participant is prompted to provide a constant identifier and a selected password. Emergency and confidential categories of medical information are identified, and the participant is prompted to provide personal information in each of the categories and a different personal identification number (E-PIN, C-PIN) for each category. The participant is also prompted to provide an instruction to disclose or to not disclose the personal information in the emergency category in the event a requester of the information is an emergency medical facility and is unable to provide the participant's E-PIN. Alteration of any of the participant's medical information is enabled upon presentation of the participant's identifier and password by the requester. The emergency information or the confidential information is disclosed upon presentation of the participant's identifier and E-PIN or C-PIN. In addition, the emergency information is disclosed to an emergency medical facility verified as such by a service provider in the event the participant has provided an instruction to disclose the emergency information. Storage and access to health related documents such as healthcare power of attorney, consent for treatment, and eyeglass prescription is also provided.

14 Claims, 4 Drawing Sheets

METHOD OF MANAGING AND CONTROLLING ACCESS TO PERSONAL INFORMATION

RELATED APPLICATION

This application claims the benefit of U.S. Provisional Application No. 60/064,332 filed Oct. 30, 1997.

BACKGROUND OF THE INVENTION

This invention relates to methods of managing personal information and of controlling access thereto, and more particularly to those methods wherein a security measure may be overruled and access to a portion of the personal information may be disclosed under specified circumstances.

One component of the effective delivery of health care is the effective management of medical information. Health care providers have recognized that effective storage, retrieval and management of medical information provides more efficient patient care. More effective management of health related information will generally cause the quality of care to increase by providing treating physicians more complete, timely and accurate information. Full and accurate knowledge of the patient's prior medical history, current medications, drug allergies, recent medical test results, etc. will typically permit the treating physician to diagnose the patient more accurately and more quickly. Additionally, effective access to such information will tend to facilitate the treating physician choosing and performing more accurately and effectively the appropriate medical procedures. Patients may not be able to speak for themselves in an emergency or unconscious condition. Even conscious and alert, many patients may not recall the specifics of their medical history and/or relevant recent treatments. Still fewer patients recall the results of their recent medical tests. Costs may also be reduced by efficient management of medical information by avoiding duplication of tests caused by lack of access to existing test data by the treating physician, or the physician's reluctance to accept the patient's recollections when serious medical consequences may result from misinformation or misdiagnosis. For such reasons, health care providers have invested considerable effort in the technologies related to the computerization and sharing, typically via fax or interactive computer networks, of such medical data and information.

Much of the previous work in connection with computerizing medical information storage and retrieval has been directed to the needs of the care provider. That is, the needs of hospitals and treating physicians have been foremost in the design and implementation of many prior art medical information systems. Recent examples of such systems include the work of Chaco (U.S. Pat. No. 5,465,082) which describes a network data storage and retrieval system for medical information as would typically be implemented in a hospital environment. In addition, the work of Whalen et. al. (U.S. Pat. No. 5,327,341) describes a computerized system for maintaining medical records and for the generation of printed reports from such stored information. Once again, the system is intended for use typically by physicians or related health care providers. The work of Coli (U.S. Pat. No. 4,31 5,309) is likewise directed towards a medical information storage, retrieval and report generating system, typically for use by treating physicians. Storage and retrieval of medical information including certain categorization techniques can be found in the work of Nematbakhsh et. al. (U.S. Pat. No. 5,572,422). Crumpler et. al. (U.S. Pat. No. 5,664,207) describe a system for the sharing of medical or other information among a plurality of users by means of data processing nodes connected temporarily and intermittently to a data processing server.

The medical data storage and retrieval information systems described above typically are developed with the needs of the health care provider in mind. Therefore, the information tends to be that appropriate for the needs of the particular physician, practice group or hospital making use of the system, omitting thereby many relevant items of personal health information. For example, provisions are not typically made in such systems for having access to the patients' living wills, organ donation wishes, authorization for treatment and other documents potentially highly relevant in the course of medical treatment, most urgently in instances when the patient is unable to speak for himself or herself. In addition, the information systems of the prior art most typically are designed for use from a limited number of known locations, typically terminals located at various locations around a treating hospital or other health care facility. Access to the medical records by the patient, or by an unforeseen and unplanned for health care provider in an emergency situation and possibly at very remote locations and at very inconvenient times of day, is not generally provided for in the prior art.

Another approach to providing medical information to the treating physician or other care provider has been to equip the individual patient with appropriate medical information to be carried on his or her person. Such information would typically be of the type that health care providers would need during an emergency situation in which the patient cannot speak for himself or herself. Such techniques include emergency medical bracelets, information cards and the like to inform treating medical personnel of the patient's important medical conditions. For economy of language, we will refer to all such devices carried on or about the patient as "on-person" medical information and medical information systems regardless of the particular medium on which such information is stored and carried.

Perhaps the most common example of such on-person data storage and retrieval is the magnetic strip on credit or similar cards used for carrying limited amounts of data relevant to the purpose for which the card is distributed. A recent example of magnetic strip technology is that of Drexler et. al. (U.S. Pat. No. 5,559,885) and the references cited therein. Such magnetic strip technology is typically used on debit or credit cards, although magnetic strips are appearing on cards for use in connection with parking garages, public transit, copy machines, etc. Such magnetic strips have proven to be a very efficient way to insure that the user has pre-paid for the service or product being delivered, debiting the account information stored on the magnetic strip with the appropriate amount, most commonly at the time the product or service is delivered. Such cards generally eliminate the need for vendor's staff to intervene in the transaction, saving transaction costs. While such cards have demonstrated their endurance and consumer acceptance in everyday commerce, they are typically quite limited in the amount of data which can be stored. Addidonally, specialized equipment is needed to alter the information appearing on the magnetic strip that is not generally available to the user of such cards (intentionally so for most cards, especially those indicating pre-payments). Both of these characteristics are serious disadvantages in using such cards for the storage of personal health information.

Other technologies are available that permit on-person storage of larger amounts of information and, in some cases, convenient alteration of this information by the user.

Examples of such on-person devices include "smart cards," which typically means a card in substantially the size and shape of a credit card with information stored thereon in the memory of a microprocessor embedded within the card. Such a smart card may include means to impede access by unauthorized parties, as is described in the work of Takahira (U.S. Pat. No. 4,960,982). An interactive, portable personal data system is described by Lessin et. al. (U.S. Pat. No. 4,868,376) in which numerous items of personal data, including health data, can be stored and carried with the individual in the form of a hand-held computer complete with keyboard and display.

On-person devices for carrying medical information as generally described above have several important drawbacks. The information must accompany the individual or patient everywhere. Continually wearing a bracelet or similar article might be too burdensome for all but the most medically concerned patients. Carrying a card requires the card to be accessible to the treating physician. In emergency situations, the patient's purse or wallet typically containing such cards might not be readily accessible to the treating physician. Also, not all medical emergencies arise with the purse or wallet on the patient's immediate person, as in swimmers, divers, or nighttime emergencies. The additional time and burden of locating such medical information during an emergency often cannot be spared, depriving the treating physician of potentially crucial medical information about the patient. If the medical information is stored on a magnetic strip, the treating physician or care provider must have access to the means to read the information. Even if the card can be promptly read, the information contained thereon is necessarily limited. Even more limited is the information stored as printed text on a medical information bracelet or card.

Not all medical information to which an individual desires access is required for emergency treatment. For example, loss or destruction of corrective eyewear requires access to the patient's prescription for replacement. Serious discomfort would occur to many eyeglass wearers until replacements can be obtained. On-person emergency medical information generally does not include eyeglass prescriptions, being constrained by limited storage capacity to the most critical and potentially life saving information.

The work of Keene (U.S. Pat. No. 5,325,294) describes a phone-in system for the storage and retrieval of information related to an individual's HIV or other medical status, date of most recent test, and frequency of inquiry. Security and authentication features are provided. The individual wishing to make use of this procedure (the "Subject") has his or her HIV test (or other medical test) entered into the computer system and receives a hologram photo-identification card with an account number printed thereon and, separate therefrom, a personal identification number ("PIN number") to be maintained in confidence by the Subject. The invention consists of a technique for the Subject to report the results of the pre-recorded test to a (presumably skeptical) individual in the company of the Subject ("Partner"). The Subject dials the computer storing his or her medical test information, entering the account number and PIN number. The phone is then handed to the Partner along with the Subject's photo-identification card. The computer system recites the account number for verification of the Subject's identity by comparison with the photo and then recites the information the Subject has authorized to be released, typically the test date, result and frequency with which the Subject makes inquiry. While this system allows phone-in access, it provides only limited medical information, requires the physical presence of the photo-identification card, and requires the participation of a conscious and at least minimally functional Subject capable of remembering his or her PIN number; conditions not always pertaining in emergency medical circumstances which are one of the important uses for the present invention.

These and similar on-person medical information storage and retrieval systems need to be updated promptly whenever the medical condition of the patient requires. For example, when prescriptions are changed by the patient's physician, such revised information must be revised on all on-person information lest the treating physician in an emergency not be aware of potentially harmful drug interactions or other conditions. Updating on-person medical information is yet another burden to be undertaken by the patient, and might easily be neglected in the activities of daily life.

Yet another drawback of on-person medical information is that it tends to be of limited extent. Only the most basic medical information can be stored on a bracelet or printed card. "Smart cards" having microprocessors and memory constructed as part of the card alleviate this situation somewhat, typically having significant storage capacity. However, smart cards typically require specialized readers to extract the information, and such readers might not be available in all emergency treatment environments. Smart cards share the disadvantages mentioned above associated with having to accompany the patient everywhere and having to be physically updated.

SUMMARY AND OBJECTS OF THE INVENTION

The present invention is a method of managing a participant's personal information and of controlling, through a service provider, access to such personal information by a requester and basically comprises the steps of prompting the participant to provide a constant identifier and a selected password; identifying a first category and a second category of the personal information; prompting the participant to provide personal information in each of the categories; prompting the participant to provide a first personal identification number (PIN-1) for the first category and a second personal identification number (PIN-2) for the second category; prompting the participant to provide an instruction to disclose or to not disclose the personal information in the first category in the event the requester is one of a defined group and is unable to provide the PIN-1 for the first category; storing the identifier, the password and the personal information in the first and second categories in a data file; storing the PIN-1 and the instruction to disclose or to not disclose in the data file in association with the first category of personal information; storing the PIN-2 in the data file in association with the First category of information; enabling alteration of any of the personal information in the data file upon presentation of the identifier and the password by the requester; disclosing the personal information in the first category upon presentation of the identifier and the PIN-1 by the requester; disclosing the personal information in the second category of the data file upon presentations of the identifier and the PIN-2 by the requester; and disclosing the personal information in the first category having an instruction to disclose associated therewith in the event the requester is unable to provide the PIN-1 for the first category and the service provider determines that the requester is one of the defined group.

A primary object of the present invention is to provide the participant with read/write access to his or her personal information, to provide requesters to whom the participant has provided the constant identifier and at least one of the PINs with read only access to the participant's personal information in the category associated with that PIN, and to provide an emergency medical facility, verified as such by the service provider, with read only access to the participant's personal information in an emergency category in the event the participant has provided advance instruction to disclose it. Additional objects and advantages of the present invention may be more readily understood in light of the following detailed description of the preferred embodiment.

DETAILED DESCRIPTION OF THE PREFERRED EMBODIMENT

Figure 1A:
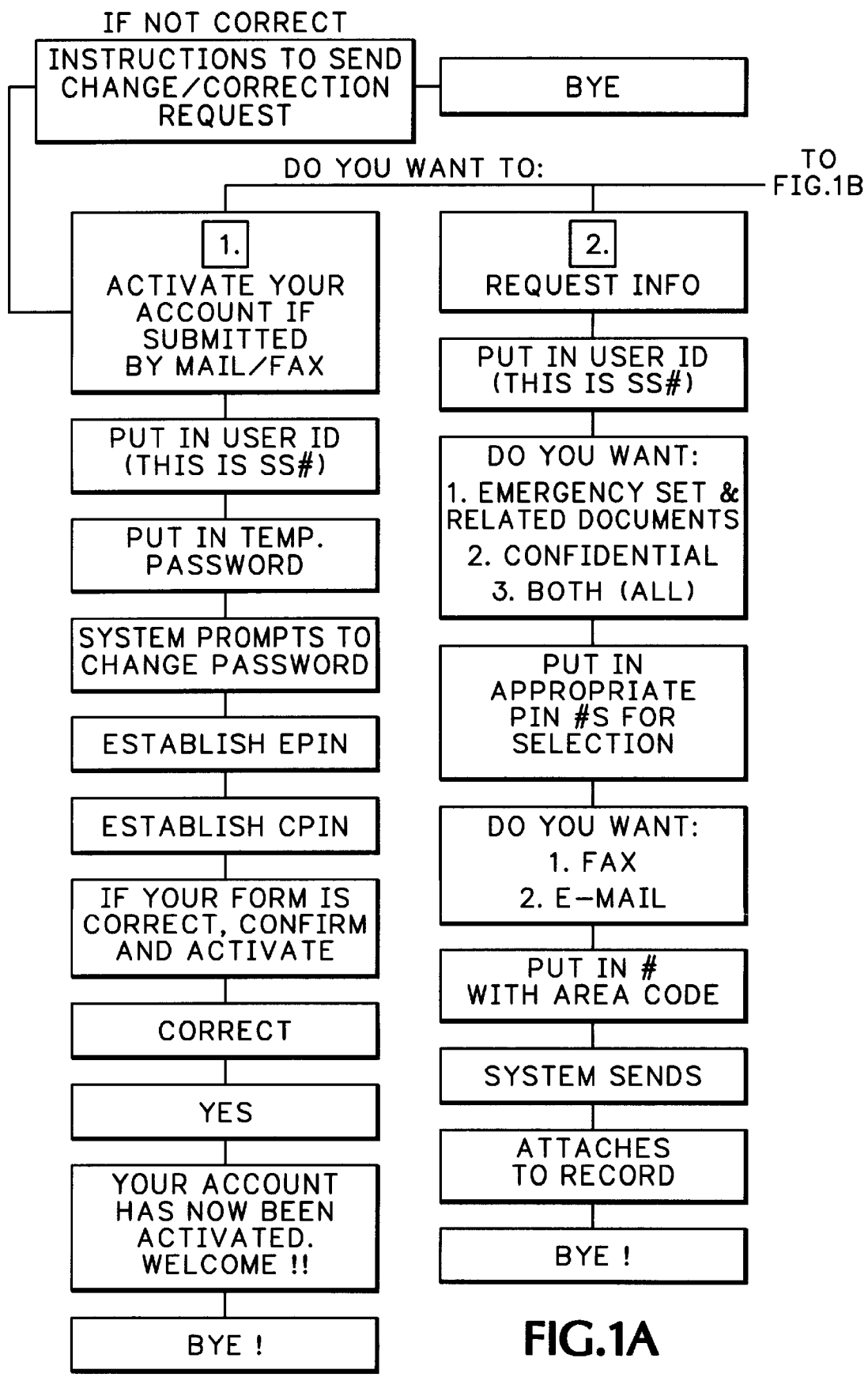
FIGS. 1A–1D is a flow chart of prompts and messages provided in the phone/fax/mail the preferred embodiment of the present invention.

As used herein, "participant" means an individual whose personal records, or whose dependent' records, are managed or are subject to being managed in accordance with the present invention, and a "requester" is anyone, including the participant, attempting to gain access to such personal records. The present method is conducted by one or more service providers to whom fees are paid by the participant, by the participant's employer or by any other party with whom the service provider may contract and through whom the participant is entitled to receive the subject services.

In its preferred form, the present method is adapted to manage a participant's medical information. Communications between the participant or requester and the service provider are conducted by various and, in some instances, by a combination of means including direct on-line interactive communication between the participant's or the requester's computer and the service provider's server and web site via a global computerized telecommunications network (hereinafter "internet communications")and/or a group comprising telephone, facsimile, Email, and postal mail (collectively "phone/fax/mail communications").

Internet Communications

The participant connects with the service organization's website (e.g. WWW.NEHDC.COM; or WWW.MEDTOUCH.NET) or some other website whose server and related hardware and software are adapted to practice the present method. The participant is prompted to indicate a desire to engage the service and having done so, is prompted to register. The registration prompts are intended to elicit from the participant a temporary password, the participant's full name, social security number, home phone number, Email address and, optionally, work phone number. The temporary password is one which the user selected at the time the participant's account was established, account establishment being a conventional process which occurs prior to registration, either via Internet communications or via phone/fax/mail communications. The participant's social security number serves as a constant identifier, by virtue of its uniqueness and relative permanence. It is contemplated that analogous government-issued, unique and permanent identifiers will be used for participants who are citizens of countries other than the United States. In addition to the foregoing information, the participant is prompted to select a new password, an emergency personal identification number ("E-PIN") and a confidential personal identification number ("C-PIN") during the registration phase. As described below in further detail, the new password in combination with the constant identifier are the keys which unlock the participant's medical information for additions, deletions or other alteration. The E-PIN in combination with the constant identifier enable disclosure of one category of the participant's medical information of particular use in medical emergencies. The C-PIN in combination with the constant identifier enable disclosure of another category of the participant's information which is of a particularly sensitive nature. Secure data transmission procedures and/or encryption may optionally be used to insure integrity and privacy of the information exchange.

Once the foregoing registration phase is completed and the participant's account is established, the participant is prompted to enter relatively specific medical information deemed to be useful in an emergency situation. The emergency information is treated by the present method as a first group or category, the entirety of which is made available for viewing and transmission, but not for addition, deletion or alteration, upon entry of the participant's constant identifier and E-PIN. The relatively specific matters in the emergency category to which the participant is prompted to provide information include, without limitation, current diagnosis, insurance coverage, physicians and other health care providers, allergies, current medications, immunizations, childhood or adult illnesses, medical hospitalizations, medical implant, and current vital statistics such as blood pressure, pulse, blood type, height and weight. The participant is then prompted to provide an instruction to disclose or to not disclose the information in the emergency category to any emergency care facility when the participant's E-PIN cannot be provided.

Once the emergency category is completed, the participant is prompted to enter relatively specific medical information deemed to be more sensitive, confidential or stigmatizing in nature than the emergency information. The sensitive information which the participant enters is treated as a second group or category, the entirety of which is made available for viewing and transmission, but not for addition, deletion or alteration, upon entry of the participant's constant identifier and C-PIN. The relatively specific matters in the sensitive or confidential category to which the participant is prompted to provide information include, without limitation, mental health history, mental health hospitalizations and drug or alcohol rehab programs, psychiatric medications, treating practitioner, blood borne contagious diseases, sexually transmitted diseases, maternal/gynecologic history, male urinary/genital/surgical procedures and other confidential health information.

Once the sensitive or confidential category is completed, the participant is prompted to indicate whether there are any health related documents to be imported into and stored in the participant's medical records. Preferably, the health related documents include one or more of the following: an authorization for blood product transfusion, an authorization to donate organs, an authorization to provide emergency medical treatment, an authorization to release medical records, a consent for transportation, a living will, a healthcare power of attorney, copies of laboratory or other tests results and a current eyeglass prescription. In addition, the participant is prompted to identify any additional documents to be provided in this category. If the documents which the participant wishes to include have been scanned into the participant's computer, they can be imported into this health related document category maintained under the present method. If the participant cannot scan the subject documents, they can be mailed or faxed to the service provider, whereupon they are scanned into the participant's file. With respect to each of the health related documents, the participant is prompted to authorize or to not authorize release of the document in the event of an emergency.

Once the participant indicates that all of the information and documents he or she wishes to enter have been accurately entered, the present method associates and stores the participant's: (a) constant identifier and new password with the medical information an d documents as a whole, (b) E-PIN with the information in the emergency category, (c) C-PIN with the information in the sensitive/confidential category, (d) instruction to disclose or to not disclose with the information in the emergency category, and (e) release indication with each of the documents authorized for release in an emergency.

To make changes to the stored information, including changes to the password, E-PIN, C-PIN, disclose/not disclose instruction, and release indications, the requester, typically the participant, visits the website and is prompted to indicate a desire to make changes and to enter the participant's constant identifier and password. The present method then presents the participant's medical record on screen and enables the requester to make any desired additions, deletions or modifications. In effect, the requester has full read-write access to all information contained in the participant's file, including the ability to change the password, E-PIN, C-PIN, disclose/not disclose instruction and release indications. Information in the emergency and/or confidential categories may be added, deleted or updated. Documents in the health related documents category may be added or deleted, all of the foregoing being in response to menu- or prompt-driven inquiries derived from the present method. The new information is displayed for verification and correction if necessary. Final approval enters and stores the additions and/or amendments as part of the permanent file for the participant. Archival storage of information deleted or superseded in the participant's data file may optionally be provided. Secure data transmission procedures and/or encryption may optionally be used to insure integrity and privacy of the information exchange.

In situations where there is a desire to view or obtain a copy of the participant's medical information in the emergency and/or confidential category, but no desire to change such information, the elements which are needed to enable the present method to disclose the information in the desired category via internet communications are the participant's constant identifier, the PIN associated with the desired category and the URL for the website in which the present method is practiced. Upon reaching the appropriate website, menu or prompt driven queries will appear which will guide the requester to enter the participant's constant identifier and E-PIN or C-PIN. The desired category of information then appears on screen for viewing and becomes available for downloading and printing. In the event the participant has authorized release of certain documents in the event of an emergency, those documents become available for viewing and downloading when the requester provides the participant's E-PIN. In the event that the participant has provided the E-PIN, C-PIN or password to a medical care provider for the purpose of disclosing or providing a copy of the information in the emergency or confidential categories or one or more documents in the health related documents category, the participant can subsequently access the website, enter the constant identifier and password, and the present method will prompt the participant to change the E-PIN, C-PIN and/or password. In this manner, the present method enables the participant to reestablish exclusive control over access to the medical information.

Preferably, the present method is fully automated with respect to internet communications involving registration, input of the participant's medical information and previously scanned health related documents, read/write access to the participant's data file when the participant's constant identifier and password are provided, and read only access when the participant's constant identifier and E-PIN or C-PIN are provided. In the foregoing operations, the security of the participant's medical information is enhanced because there is no need for any representative of the service provider to become involved. From the service provider's perspective, such automation reduces labor costs and the potential for human error.

Nevertheless, in the following situation, the present method requires some human intervention on the service provider's part. In those emergency situations where the participant is too disabled to provide his or her E-PIN, the health care provider may still be able to obtain the participant's constant identifier and the URL for the service provider's website. The present method preferably includes the steps of issuing an identification card to the participant and encouraging the participant to carry this card and the participant's constant identifier (i.e., social security number) at all times. It is believed that in emergency situations of this type, medical care givers are entitled to search for and to examine any information which the disabled person may be carrying on his or her person and which may be of assistance in treatment. The identification card prominently indicates that the participant has stored medical information that may be of use in an emergency. The subject card also bears the service provider's website address and telephone number, the participant's name and address and, optionally, the participant's constant identifier. Even though the emergency medical facility cannot provide the participant's E-PIN information, the emergency facility can log onto the service provider's website, whereupon the present method prompts the emergency facility requester to provide the participant's constant identifier, to indicate that the participant has a medical emergency and cannot provide the E-PIN and to provide identifying and communications information concerning the emergency facility. The present method then alerts one of the service provider's representatives that an emergency exists and provides the representative with the information provided by the emergency facility requester. The service provider's representative then attempts to verify that the emergency facility requester is in fact such a facility. Verification of the medical facility's identity under the present method is accomplished by cross checking the identifying information provided by the requester with a previously established data file of recognized emergency care facilities and/or by calling the telephone number provided by the requester and asking questions intended to elicit responses indicative of a bona fide emergency care facility. If the medical facility's identity is verified, the service provider's representative attempts to access the participant's data file to the extent of determining whether the participant has provided an instruction to disclose any information or documents in the event of an emergency in which the participant's E-PIN cannot be provided. If there is an instruction to disclose, the service provider's representative enters an authorization code which enables disclosure of the information in the emergency category and of the authorized documents to the emergency medical facility via internet communications or fax.

Phone/fax/mail

The present method of managing a participant's medical records may be accomplished by various combinations of telephone, fax, E-Mail and postal mail communications. At the outset, the participant may request paper forms and provide account information by calling a representative of the service provider at a well publicized telephone number, or the service provider's representative may make the forms available to participants in person in connection with seminars and meetings sponsored by the participant's employer or other organization with whom the service provider may contract. The paper forms prompt the participant to provide emergency and confidential health information and health related documents as described above in connection with internet communications. In addition, the paper forms prompt the participant to provide an instruction to disclose or to not disclose the information in the emergency category in the case of an emergency where the participant is unable to provide the E-PIN. The participant is also prompted with respect to each health related document to authorize or to not authorize release in the event of an emergency. The participant is also prompted to provide a temporary password and a constant identifier, typically the participant's social security number. The participant sends the completed form and copies of any health related documents to the service provider, either by mail or fax. The service provider then enters the participant's emergency and confidential information and scans the health related documents into the participant's data file. The participant's temporary password and constant identifier are associated with the data file as a whole, the instruction to disclose/not disclose is associated with the emergency category and the release instruction is associated with each of the health related documents authorized for release in an emergency. Next, a copy of the data file as entered is sent to the participant via fax or mail. The participant reviews the data file as entered for accuracy and returns any corrections, additions or modifications by fax or mail. The review/revision process is repeated until the participant is satisfied that all information and documents as entered are complete and accurate. As illustrated in FIG. 1A, Column 1, when the participant is satisfied with the data file as entered, the participant telephones a designated number and is prompted via automated voice instructions to enter via touch tone the constant identifier and temporary password and to establish the participant's new password, E-PIN and C-PIN and to confirm and activate the participant's data file. The present method associates the touch tone-entered new password with the participant's data file as a whole and associates the touch tone-entered E-PIN and C-PIN with the emergency and confidential information categories, respectively.

As illustrated in FIG. 1A, Column 2, the present method provides access via phone/fax/mail to the confidential or emergency categories of data, and to the documents in the health related documents category in the following manner. The requester telephones the designated phone number and is prompted via automated voice instructions to enter via touch tone the participant's constant identifier and to indicate which category or categories of information and documents are requested. The requester is then prompted to enter the appropriate E-PIN and/or C-PIN and to provide a fax number or E-Mail address to which a copy of the requested information and/or documents are to be transmitted. The present method then transmits the requested information and enters in the participant's data file the recipient's fax number or E-Mail address, the date of transmission and the category transmitted. In this manner, the present method keeps a record of the transmission readily accessible to the participant.

Figure 1B:
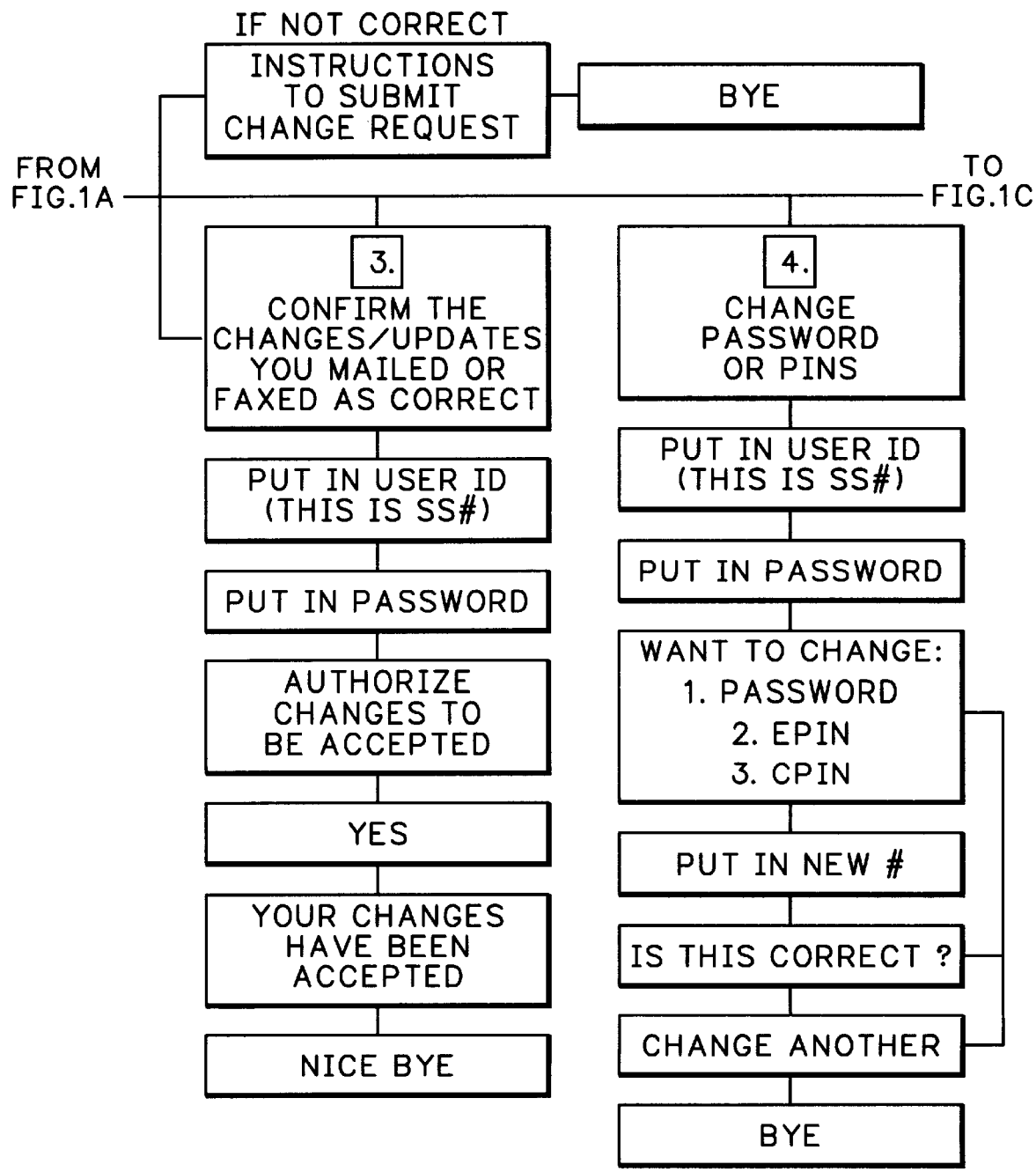

To make changes to the stored information via phone/fax/mail, the present method provides the participant with a paper "Change" form, either upon the participant's phone request or during the course of establishing the participant's account. The participant makes the desired additions, deletions or alterations on the Change form and sends it via fax or mail to the service provider, whereupon the indicated changes are provisionally entered in the participant's data file. A copy of the data file, as provisionally modified, is sent to the participant via fax or mail, and the above-described review/revision process is followed in connection with these modifications. The present method then instructs the participant to place a telephone call to the designated phone number when the participant is satisfied that all modifications are complete and accurate. As illustrated in FIG. 1B, Column 3, upon placing the call, the participant is prompted to enter his or her constant identifier and password and to confirm that the data file as modified is complete and accurate, whereupon the data file as provisionally modified is activated.

As illustrated in FIG. 1B, Column 4, the present method preferably includes steps by which the participant's password, E-PIN and/or C-PIN may be changed over the telephone. The designated telephone number is called, and the caller is prompted to enter the participant's constant identifier and current password. The caller is then prompted to indicate which of the password, C-PIN or E-PIN is to be changed. The new password, C-PIN or E-PIN is then entered and the caller is prompted to confirm the new entry. A voice prompt is then given for the caller to indicate whether another of the selected security codes is to be changed and the steps of prompting the caller to indicate which code is to be changed, to indicate the new code and to confirm its correctness are repeated. In this manner, the present method enables the participant to quickly terminate access after disclosing one of the security codes or to change codes simply as a matter of preventive maintenance.

Figure 1C:
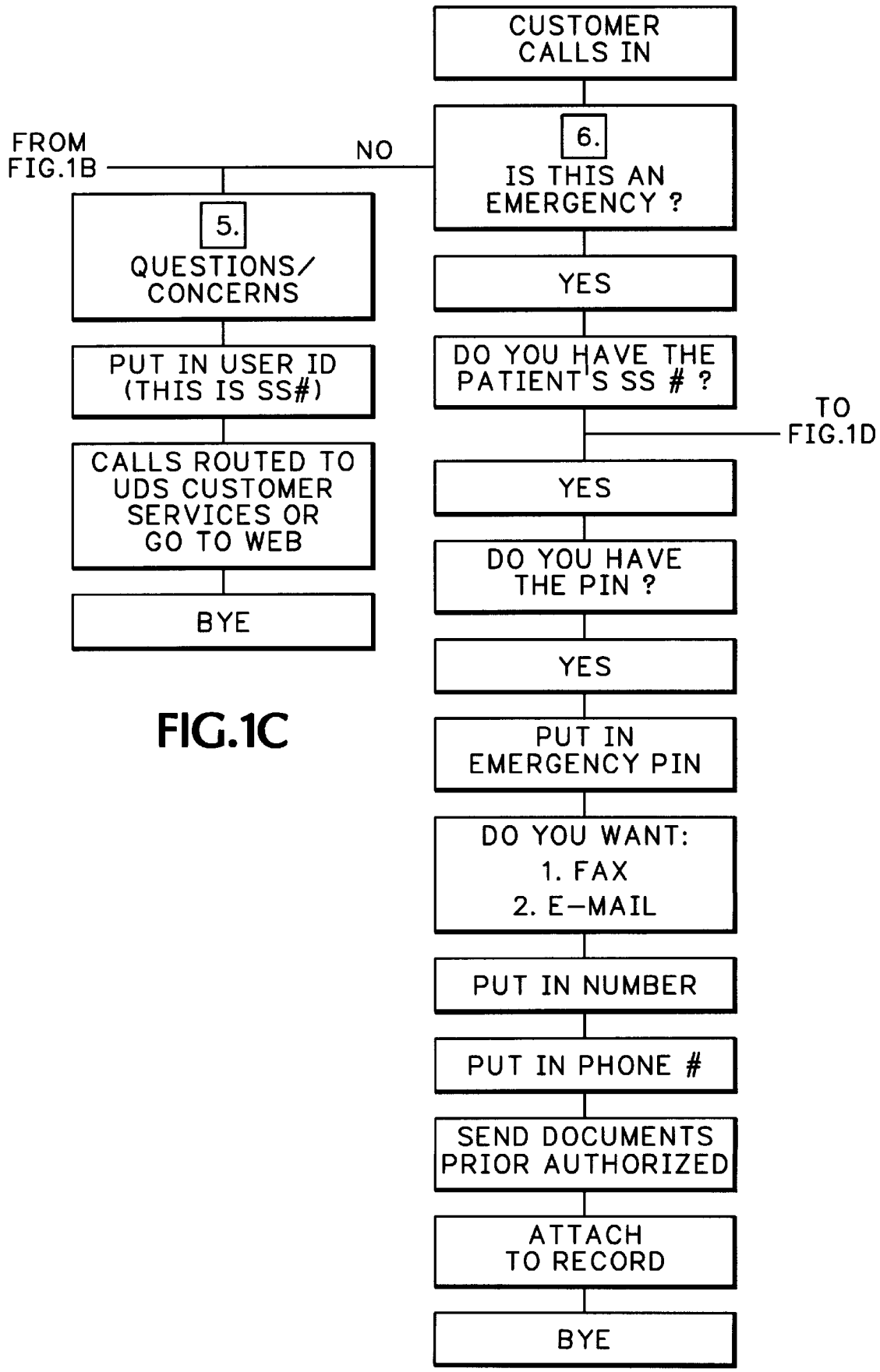

As illustrated in FIG. 1C, Column 5, the present method provides the caller with the option of speaking to someone in the service provider's customer service department concerning matters which do not fall within one of the topics stated at the outset of the phone call. In order to do so, however, the caller must provide a participant's constant identifier. In this manner, the present method substantially limits its service via the designated phone number to participants and to those requesters who know the participant's constant identifier, thereby reducing the chances of its telephone lines and/or customer service representatives being tied up by nonparticipant matters.

Figure 1D:
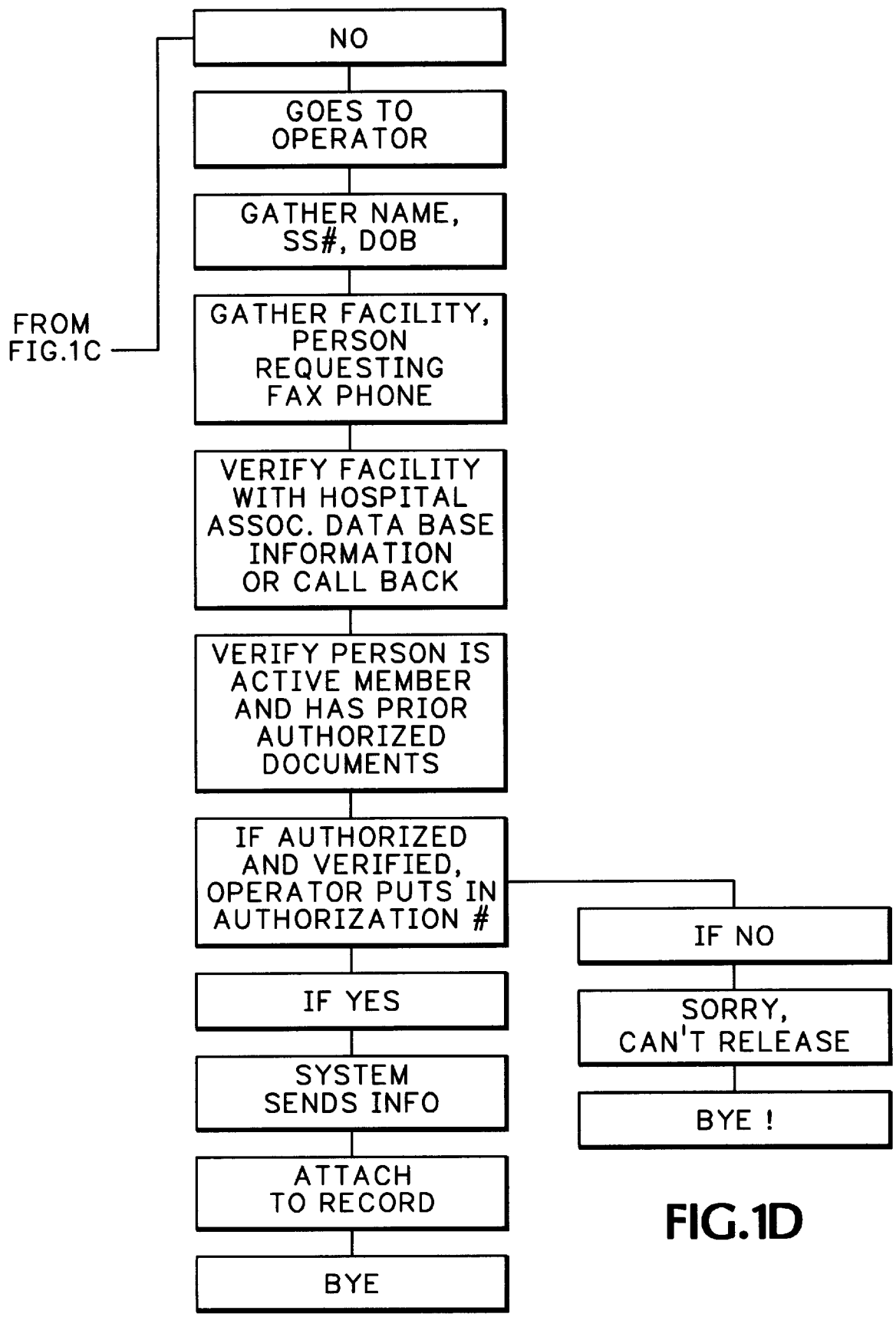

As illustrated in FIGS. 1C and 1D, dual-Column 6, the present method provides access to the participant's emergency category information and emergency-authorized documents via phone/fax/mail under certain circumstances. Preferably, the first question asked when the designated telephone number is called is whether an emergency situation exists. If the response is no, the previously discussed options illustrated in Columns 1–5 are presented. If the answer is yes, the prompts and elements presented in dual-column 6 are engaged. The first prompt is for the participant's constant identifier, however, since it is anticipated that many of the requesters who indicate an emergency will not be familiar with the present method, the prompt is an express request for the patient's social security number. Next, the requester is prompted to enter the participant's (patient's) emergency PIN. If the requester enters the E-PIN, the present method prompts the requester to select fax or E-Mail transmission and to provide the requester's fax number or e-mail address. The participant's medical information in the emergency category and the related health documents for which the participant has authorized release in an emergency are then transmitted to the fax number or E-Mail address provided and a record of the transmission is made in the participant's data file.

A requester who does not have the participant's emergency PIN responds in the negative to the subject prompt, whereupon the present method connects the requester to a customer service representative. The service provider's representative takes the patient's name, date of birth and social security number from the requester, together with the requester's name, the name of the requester's emergency medical facility and its fax and phone numbers. The service representative then attempts to verify the emergency facility through accessible listings and other records concerning such facilities and/or by dialing the phone number given by the requester to determine if responses to various questions are indicative of an emergency facility. Either during or after verification, the customer service representative determines whether there is a participant corresponding to the patient information provided by the requester and, if so, the representative determines whether the participant has provided an instruction to disclose in the event of an emergency. If the service representative verifies the emergency facility, locates the participant file corresponding to the patient information and finds an instruction to disclose, the representative enters an authorization number and the fax number or E-Mail address previously provided by the caller, whereupon the present method automatically faxes the participant's information in the emergency category and the documents authorized for release to the emergency facility.

The preferred embodiment of the present invention is intended to be delivered in the English language and makes use of identification means (typically social security number) directed generally to users in the United States. However, it is within the scope of the present invention that access in multiple languages be provided, typically in response to prompts or menus mad e available to the user upon initial contact or inquiry. Translation of the information to various languages is contemplated within the scope of the present invention, as is the use of personal identifiers appropriate to non-United States users of the present system (e.g. national health insurance information, passport data, citizen identifying numbers, etc.)

The foregoing detailed description of the preferred embodiment is not intended to limit unduly the spirit of the invention or the scope of the following claims.

What is claimed is:

1. A method of managing personal information concerning a participant and of controlling, in conjunction with a service provider, access to said personal information by a requester, said method comprising the steps of:

prompting the participant to provide a constant identifier and a selected password;

identifying a first category and a second category of the personal information;

prompting the participant to provide personal information in each of the categories;

prompting the participant to provide a first personal identification number (PIN-1) for the first category and a second personal identification number (PIN-2) for the second category;

prompting the participant to provide an instruction to disclose or to not disclose the personal information in the first category in the event the requester is one of a defined group and is unable to provide the PIN-1 for said first category;

storing the identifier, the password and the personal information in the first and second categories in a data file;

storing the PIN-1 and the instruction to disclose or to not disclose in the data file in association with the first category of personal information;

storing the PIN-2 in the data file in association with the second category of personal information;

enabling alteration of any of the personal information in the data file upon presentation of the identifier and the password by the requester;

disclosing the personal information in the first category of the data file upon presentation of the identifier and the PIN-1 by the requester;

disclosing the personal information in the second category of the data file upon presentation of the identifier and the PIN-2 by the requester; and disclosing the personal information in the first category having an instruction to disclose associated therewith in the event the requester is unable to provide the PIN-1 for said first category and the service provider determines that said requester is one of the defined group.

2. The method according to claim 1, wherein the step of disclosing the personal information in the first category having an instruction to disclose associated therewith further comprises disclosing said information upon presentation of an authorization code by the service provider.

3. The method according to claim 1, wherein each of the first and second categories comprises a plurality of items.

4. The method according to claim 3, wherein the first category comprises items of potential significance in a medical emergency.

5. The method according to claim 4, wherein the defined group comprises emergency medical facilities.

6. The method according to claim 4, wherein the first category comprises a plurality of items in a group comprising the participant's emergency contact person, current diagnosis, primary insurance, physicians, allergies, current medications, immunizations, illnesses, hospitalizations, surgeries, and medical implants.

7. The method according to claim 3, wherein the second category comprises items of a particularly sensitive or potentially stigmatizing nature.

8. The method according to claim 7, wherein the second category comprises a plurality of items in a group comprising the participant's mental health history, mental health hospitalizations /drug or alcohol rehab programs, psychiatric medications, treating practitioner, blood borne contagious diseases, sexually transmitted diseases, maternal/gynecologic history, and male urinary/genital/surgical procedures.

9. The method according to claim 1, which further comprises the steps of:

prompting the participant to provide one or more documents containing personal information not included in the first or second categories;

prompting the participant to provide an indication for each of the documents as to whether the participant desires the service provider to release said document to the requester in a specified circumstance;

storing the indication in association with the document in the data file; and disclosing to the requester in the specified circumstance the document having the indication to release associated therewith.

10. The method according to claim 9, wherein the participant is prompted to provide one or more documents containing health related information or instructions relating to medical treatment.

11. The method according to claim 10, wherein the specified circumstance for release of the document comprises a medical emergency.

12. The method according to claim 1 which further comprises the step of providing an internet communications site for accomplishing the other steps of said method.

13. The method according to claim 1, which further comprises the steps of providing one or more paper forms for identifying the first and second categories of the personal information, for prompting the participant to provide the personal information in each of said categories, for prompting the participant to provide the instruction to disclose or to not disclose, for enabling alteration of any of the personal information; and for disclosing the personal information in the first or second categories; and providing automated telephone communications for prompting the participant to provide the constant identifier and the selected password, for prompting the participant to provide the PIN-1 and the PIN-2, for presentation of the identifier and password by the requester, for presentation of the identifier and PIN-1 by the requester, for presentation of the identifier and PIN-2 by the requester and for connecting the requester to a representative of the service provider for voice communications.

14. The method according to claim 13, which further comprises the step of prompting the requester via the automated telephone communications to provide a fax number or an E-Mail address and wherein the step of disclosing the personal information in the first category comprises faxing or E-Mailing the personal information in the first category upon presentation of the identifier, the PIN-1 and the fax number or E-Mail address by the requester and the step of disclosing the personal information in the second category comprises faxing or E-Mailing the personal information in the second category upon presentation of the identifier, the PIN-2 and the fax number or E-Mail address by the requester.

* * * * *